United States Patent [19]

Lewin et al.

[11] 3,937,799

[45] Feb. 10, 1976

[54] RADIOASSAY OF VITAMIN B-12 EMPLOYING BENTONITE

[75] Inventors: Nathan Lewin, Corte Madera; James E. Fries, Novato; C. Steven Richards, Vallejo, all of Calif.

[73] Assignee: Bio-Rad Laboratories, Richmond, Calif.

[22] Filed: Aug. 26, 1974

[21] Appl. No.: 500,967

[52] U.S. Cl. .................................. 424/1; 23/230 B
[51] Int. Cl.$^2$ ..................... G01N 31/00; G21H 5/02
[58] Field of Search ....................... 424/1; 23/230 B

[56] References Cited
UNITED STATES PATENTS
3,442,819   5/1969   Herbert ............................. 424/1 X
FOREIGN PATENTS OR APPLICATIONS
697,060   9/1953   United Kingdom ................. 424/1 X

OTHER PUBLICATIONS

Hall et al., *Radioisotopes in Medicine: in Vitro Studies*, U.S. Atomic Energy Commision, June, 1968, pp. 365–379.

Primary Examiner—Benjamin R. Padgett
Assistant Examiner—Christine M. Nucker
Attorney, Agent, or Firm—Townsend and Townsend

[57] ABSTRACT

Radioassay for vitamin B-12 using the unknown quantity of non-radioactive vitamin B-12 released from serum mixed with the radioactivity of a known quantity of radioactive vitamin B-12 tracer. A solution of intrinsic factor having a binding capacity less than the quantity of serum vitamin B-12 and radioactive vitamin B-12 is used to bind a portion of the vitamin B-12 mixture. The vitamin B-12 not bound to intrinsic factor is removed by addition of a bentonite-containing tablet. The quantity of radioactive vitamin B-12 bound to intrinsic factor is compared with standard values and the unknown serum vitamin B-12 obtained.

In the steps of the procedure the acid assay medium is pre-combined with the radioactive tracer so that the radioactive vitamin B-12 tracer receives the same treatment as serum vitamin B-12. Certain of the other reagent solutions are pre-combined and the concentration of the components adjusted so that the volume used of each of these other reagent solutions is the same in different assay steps. Thus, fewer pipetting steps are necessary.

7 Claims, 1 Drawing Figure

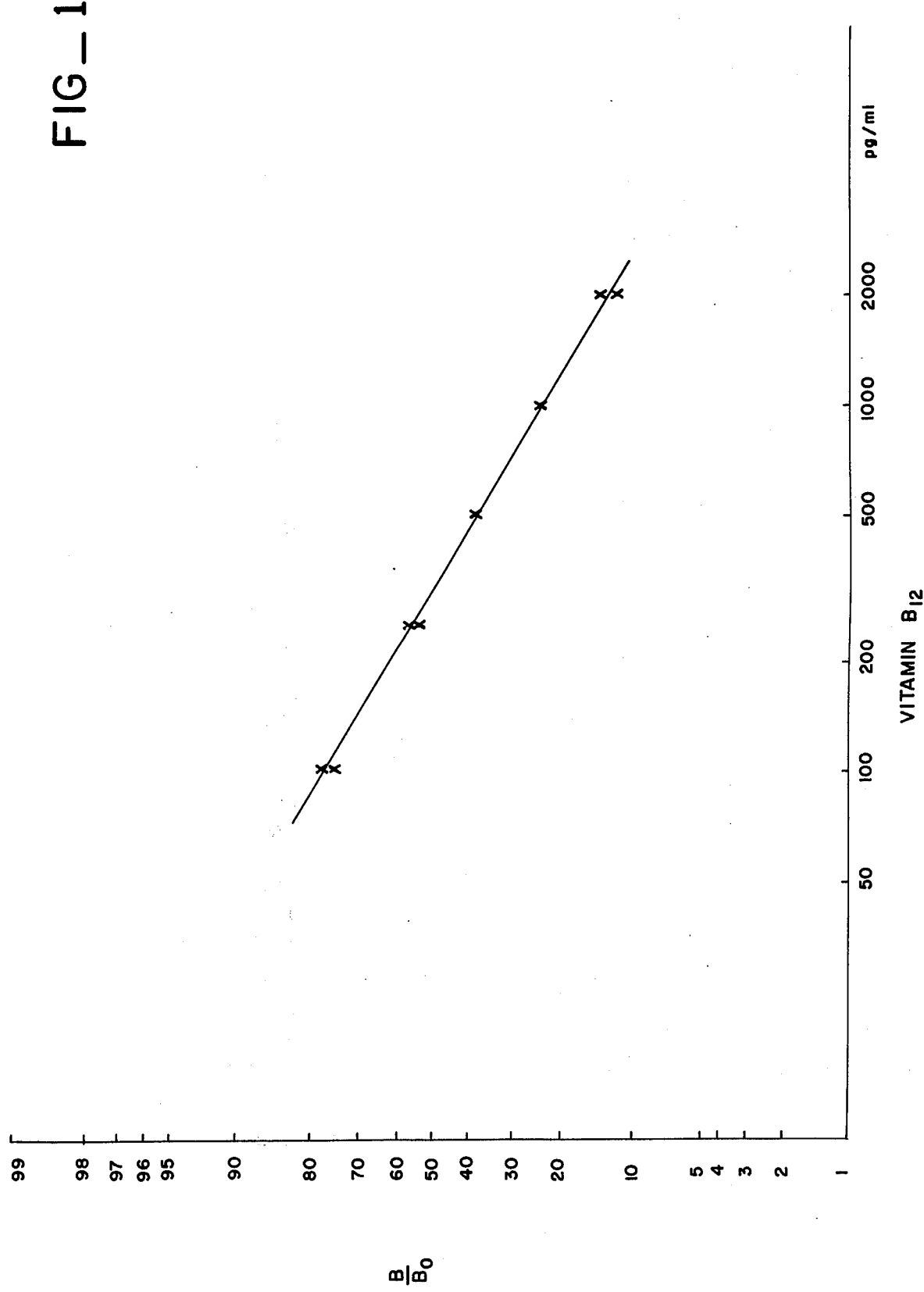
FIG_1

RADIOASSAY OF VITAMIN B-12 EMPLOYING BENTONITE

BACKGROUND OF THE INVENTION

1. Field of the Invention

This invention relates to the radioassay for vitamin B-12. More particularly, the invention relates to a radioassay for vitamin B-12 using the principle of radioisotope dilution in which improved techniques for the separation of vitamin B-12 not bound by intrinsic factor (IF) are provided as well as novel formulation of reagent solutions and their order of addition to achieve a more rapid and simpler method than those heretofore used in analogous assay procedures.

2. Description of the Prior Art

Principles of the methods to which the present improvements are directed are taught in the following references:

Lau, K.-S. Gottlieb, C. W., Wasserman, L. R., and Herbert, V., Measurement of Serum Vitamin B-12 Level Using Radioisotope Dilution and Coated Charcoal. Blood 26, 202 (1965)

Herbert, V., Gottlieb, C. W., and Lau, K.-S, Hemoglobin-coated Charcoal Assay for Serum Vitamin B-12. Blood 28, 130 (1966)

U.S. Pat. No. 3,442,819.

In particular, the principle of the present assay known as radioisotope dilution is described in Example IX of said U.S. Pat. No. 3,442,819. In this procedure the serum vitamin B-12 and radioactive vitamin B-12 compete for limited binding capacity of IF. The portion of the radioactive vitamin B-12 and serum vitamin B-12 not bound must be removed. A number of previously reported methods of removing or separating the bound from the free vitamin B-12 are reported in the following:

Dialysis

Barakat, R. M., and Ekins, R. P. (1963). An Isotopic Method for the Determination of Vitamin B-12 Levels in Blood, Blood 21, 70–79

Friedner, S., Josephson, B., and Levin, K. (1969) Vitamin B-12 Determination by Means of Radioisotope Dilution and Ultrafiltration. Clin. Chim. Acta 24, 171–179

Diethylaminoethyl (DEAE) Cellulose

Frenkel, E. P., Keller, S., and McCall, M. S. (1966) Radioisotopic Assay of Serum Vitamin B-12 with the Use of DEAE Cellulose, J. Lab. Clin. Med. 68, 510–522

Tibbling, G. (1969). A Method for Determination of Vitamin B-12 in Serum by Radioassay; Clin. Chim. Acta 23, 209–218

Protein Coated Charcoals

Lau, K. S., Gottlieb, C. W., Wasserman, L. R. and Herbert, V. (1965) Measurement of Vitamin B-12 Level Using Radioisotope Dilution and Charcoal, Blood 26, 202–214

Herbert, V., Gottlieb, C. W. and Lau, K. S. (1966) Hemoglobin-coated Charcoal Assay for Serum Vitamin B-12, Blood 28, 1930–132

Raven, J. L., Walker, P. L., and Barkham, P. (1966) Comparison of the Radioisotope Dilution-coated Charcoal Method and a Microbiological Method (L. leichmanni) for Measuring Vitamin B-12 in Serum. J. Clin. Path. 19 610–613

Herbert, V., U.S. Pat. 3,442,819 (1969)

Precipitation of Bound Vitamin B-12

Rothenberg, S. P. (1963), Radioassay of Serum Vitamin B-12 by Quantitating the Competition Between $Co^{57}$ B-12 and Unlabelled B-12 for the Binding Sites of Intrinsic Factor. J. Clin. Invest. 42, 1391–1398

Sephadex

Wide, L. and Killander, A. (1971). A Radiosorbent Technique for the Assay of Serum Vitamin B-12. Scand. J. Clin. Lab. Invest. 27, 151–159

Solid Phase-bound Intrinsic Factor

Cesca, M., and Lundkvist, U., Use of Solid Phase Intrinsic Factor for Radiosorbent Assay of Vitamin B-12. Clin. Chim. Acta 32 (1971) 339–354

Ion Exchange Resins

Brombacher, P. J., Gijzen, A. H. J., and Soons, M. P. J., A Systematic Investigation on the Assay of Vitamin B-12 in Serum by Radioisotope Dilution, Clin. Chim. Acta 36 (1972) 493–498

Roos, P., in Symposium on "in vitro" Procedures with Radioisotopes in Clinical Medicine, Vienna 1969. IAEA-SM-124/27.

All of these prior separation techniques have certain disadvantages. Thus, the use of charcoal solutions has detrimental effects as reported in "The Separation of Free and Bound Vitamin B-12", British Journal of Haematology, J. F. Adams and Fiona C. McEwan, 1974, 26, 581. In addition, the main disadvantages of charcoal suspensions is non-homogeneity of dose and introduction of additional suspension-carrying volume of fluid into each tube. Column methods also require time consuming elution, and may generate larger quantities of radioactive waste. Gel exclusion columns require exactly reproducible configuration, with respect to geometry and flow rate. Solid phase systems such as immobilized IF (such as those commercially available from Pharmacia) require prolonged agitation (about three hours) of a solid/liquid system and subsequent washing of the solid support to remove occluded material during centrifugation.

Substantially all of the foregoing difficulties are avoided by the present process in which bentonite, preferably in the convenient form of a pre-measured tablet, is utilized to adsorb unbound radioactive and serum vitamin B-12. This adsorbent is easily separated from the assay media by centrifugation, and results in uniformly high recoveries.

SUMMARY OF THE INVENTION

In accordance with the present invention, serum vitamin B-12 and radioactive vitamin B-12 tracer compete for IF of limited binding capacity, i.e., less binding capacity than required to bind all of the serum and radioactive vitamin B-12. Thereafter, free radioactive vitamin B-12 and free serum vitamin B-12 are separated from IF-bound vitamin B-12 prior to measuring radioactivity for reference with a curve constructed by the use of vitamin B-12 standards. The separation of free vitamin B-12 and free serum vitamin B-12 from the radioactive vitamin B-12 and serum vitamin B-12 bound thereto is executed by adding an effective amount of bentonite to adsorb free radioactive vitamin B-12 and free serum vitamin B-12 whereby the sample solution of IF with bound radioactive vitamin B-12 and serum vitamin B-12 can be physically segregated from solid bentonite with adsorbed free vitamin. Thus, the radioactivity in liquid phase is proportional to the quantity of bound vitamin. The amount of bentonite added per assay tube is not critical provided that each tube receives the same quantity, hence, the advantage of tabletting this mineral. A 10 mg tablet (not including inert carrier cellulose) is convenient for the sample size used.

Other novel and advantageous aspects of the present improved assay relate to the pre-combination of the acid assay media and the radioactive tracer. This and other combined reagents described below produce an overall convenience to the technician practicing the assay. In the instance of this combination of assay media and tracer, the desirable result is that the radioactive tracer undergoes the same treatment as the serum vitamin B-12. Other reagent solutions utilized include: HSA pre-combined with standards, HSA pre-combined with IF, and a cyanide reagent. The acid medium in conjunction with the cyanide reagent and the heat step effect the release of vitamin B-12 and denaturation of indigenous binders. The latter reagents are so formulated with respect to concentration of the components as to permit the use of the same volume of each of the reagent solutions in performing the assay. This means that all reagent solutions other than the combined acid assay medium and tracer solution can be measured with the same size pipette. The number of fluid measurements is reduced and extremely simplified for the technician.

BRIEF DESCRIPTION OF THE DRAWING

FIG. 1 is a plot of a standard curve for use in the present assay. Values obtained from unknown serum can be applied to the curve to find serum vitamin B-12 concentrations.

DESCRIPTION OF THE PREFERRED EMBODIMENTS

Example I: Practice of the Radioactive Assay Procedure

The following reagents are utilized:

Reagent 1 is a tablet containing 10 mg of bentonite, inert binder and cellulose.

Reagent 2 is intrinsic factor made up at 20 mg/100 ml $H_2O$ and filtered and to which human serum albumin (HSA)* has been added. (0.70 ± 0.01 grams HSA per 100 ml sterile water.) It is adjusted to give $B_o$ of 50% (approximately). (Greater dilution may be required if $B_o > 50\%$. See calculation No. 9 below for definition of $B_o$.)

*HSA solutions contain 0.001% thimerosal preservative.

Reagent 3** is 20% 0.25 ± 0.02 N HCl and 80% 0.9% NaCl in water. Vitamin B-12 $Co^{57}$ is added to this medium prior to use and is adjusted to give 65 ± 3 pg/ml.

**Other media which may alternatively be used are: (i) 1M acetic acid (ii) 0.5M acetic acid (iii) 0.25M glycine buffer, pH 3.4

In general, whichever acid or buffer is selected, it is used in an amount to generate a pH of about 1.9 - 3.5 in the media after reaction between the assay media, serum and IF. The results obtained with the acetic acid and glycine buffer as a releasing agent for vitamin B-12 are similar to those obtained by the use of HCl/saline.

Reagent 4 is potassium cyanide (0.05 mg/ml) and is prepared as follows: dissolve 100–105 mg of potassium cyanide in sterile water, add 2.0 ml of 0.1 N sodium hydroxide (4 g NaOH/liter) and make up to 1000.0 ± 0.1 ml with sterile water. Dilute 1:1 for working dilution.

The assay steps may be as follows (mixing after each addition):

1. A series of test tubes are labelled 1 through N. To each tube add 1 ml of Reagent 3.
2. To tubes 1 and 2 add 200 ul of Standard A and to tubes 3 through 7 add 200 ul of Standards B through F.
   a. Standard A is O pg Vitamin B-12/ml
   b. Standards B through F are
   $B = 100$ pg B-12/ml; $C = 250$ pg B-12/ml
   $D = 500$ pg B-12/ml; $E = 1,000$ pg B-12/ml
   $F = 2,000$ pg B-12/ml
3. To tubes 8 through N et. seq. add 200 ul of unknown sera.
4. Add to all tubes 200 ul of Reagent 4.
5. All test tubes are placed in 100°C water bath for 15 minutes.
6. Remove tubes and cool to room temperature, add 200 ul of Reagent 2 to tubes 2 through N et. seq. Allow to stand 30 minutes at ambient room temperature. Do not add any Reagent 2 to Tube 1.
7. At the end of 30 minutes add 1 adsorbent tablet (Reagent 1) to each tube. Vortex each tube 10 seconds, allow to stand 5 minutes and centrifuge for 10 minutes or sufficient time and sufficient number RPM, e.g., 2500, to pack the adsorbent thoroughly.
8. The supernatant is decanted into counting vials and counted on a suitable instrument.
9. Calculations:

$B/B_o$ is calculated $B = $ amount of radioactivity in the supernate of the serum or standard tube minus the radioactivity in the supernate of the blank tube $B_o = $ amount of radioactivity in the supernate of the zero standard tube minus the radioactivity in the supernate of the blank tube $$\frac{B}{B_o}\text{(Percent tracer bound as \% zero standard)} = \frac{\text{cpm tube No. } N \text{ (or standards)} - \text{cpm tube No. 1}}{\text{cpm tube No. 2} - \text{cpm tube No. 1}} \times 100$$

Standard Curve:

Plot $B/B_o$ versus pg/ml value of standards A to F, for example on logit/log paper.

Unknowns

Read pg/ml from standard curve using $B/B_o$ values obtained above.

REAGENT ADDITION CHART

| Tube No. | Tracer (ml) | Standard or Serum (ul) | KCN (ul) | Intrinsic Factor (ul) |
|---|---|---|---|---|
| 1 Blank | 1 | 200 | 200 | — |
| 2 Trace Binding | 1 | 200 | 200 | 200 |
| 3–7 Standards | 1 | 200 | 200 | 200 |
| 8–N Sera | 1 | 200 | 200 | 200 |

Boil 15 min.

Utilizing the above procedure, the following data was collected and is shown below in Table 1. The standard values were used to plot the graph shown in FIG. 1:

TABLE 1

| Tubes | Sample | CPM | CPM-Blank | Bound as % of Trace Binding (O Std.) | Vitamin B-12 in Picograms/ml From Graph |
|---|---|---|---|---|---|
| 1A | Blank Tubes | 91) | | | |
| 1B | | 128) 110 | | | |
| 2A | Trace Binding (O Standard) | 5775 | 5665) )5640 | 100% | |
| 2B | | 5725 | 5615) | | |
| 3A | 100 picogram/ml standard | 4420 | 4310 | 76.4% | |
| 3B | | 4506 | 4396 | 77.9% | |
| 4A | 250 picogram/ml standard | 3221 | 3111 | 55.2% | |
| 4B | | 3292 | 3182 | 56.4% | |
| 5A | 500 picogram/ml standard | 2314 | 2204 | 39.1% | |
| 5B | | 2343 | 2233 | 39.6% | |
| 6A | 1000 picogram/ml standard | 1454 | 1344 | 23.8% | |
| 6B | | 1464 | 1354 | 24.0% | |
| 7A | 2000 picogram/ml standard | 816 | 706 | 12.5% | |
| 7B | | 887 | 777 | 13.8% | |
| 8A | Serum unknown No. 1 | 1800 | 1690 | 30.0% | 740 picograms/ml |
| 8B | | 1812 | 1702 | 30.2% | 730 picograms/ml |
| 9A | Serum unknown No. 2 | 2697 | 2587 | 45.9% | 385 picograms/ml |
| 9B | | 2569 | 2459 | 43.6% | 420 picograms/ml |

Example II: Superiority of Bentonite Adsorbent

To demonstrate the superior performance of bentonite in the removal of free vitamin B-12 from the reaction medium, the following work was done:

To 1.0 ml of solution containing 0.20 ml of 0.255 N HCl, 0.80 ml of 0.9% NaCl and 65 pg of Vitamin B-12 -Co 57 (100 uCi/$\mu$g) was added 0.20 ml of pooled serum. This was followed by 0.20 ml of KCN solution (10 $\mu$g KCN) and heating for 15 minutes at 100°C.

After cooling to room temperature, in each case, 0.010 gm of a silicate-mineral was added and the tubes were vortexed for 10 seconds. The supernatant was counted for 1 minute after centrifugation at 2,900 rpm for 10 minutes.

Positive controls were extracted with
i. *Tetra-Count tablets
ii. Charcoal 10 mg/0.8 ml of 0.9% NaCl

*Tetra-Count tablets are commercially available tablets containing 10 mg of bentonite and are available from Bio-Rad Laboratories, Richmond, California.

| Mineral | Percent of Total Radioactivity Recovered |
|---|---|
| Dickite | 3.1 |
| Pyrophyllite | 2.7 |
| Metabentonite (potash bentonite) | 13.8 |
| Kaolinite | 7.2 |
| Attapulgite | 24.3 |
| Florisil | 38.1 |
| Bentonite | 99.6 |
| Controls | |
| Tetra-Count tablet | 99.2 |
| Charcoal suspension | 98.0 |

What is claimed is:

1. In the method for the radioassay of vitamin B-12 in a serum sample solution in which a radioactive vitamin B-12 tracer and serum vitamin B-12 compete for intrinsic factor (IF) of limited binding capacity, and thereafter free radioactive vitamin B-12 and free serum vitamin B-12 are separated from IF and the radioactive vitamin B-12 and serum vitamin B-12 bound thereto prior to measuring radioactivity for reference to standard values, the improvement comprising separating free radioactive vitamin B-12 and free serum vitamin B-12 from IF and the radioactive vitamin B-12 and serum vitamin B-12 bound thereto by adding an effective amount of bentonite to adsorb free radioactive vitamin B-12 and free serum vitamin B-12 whereby the supernatent solution of IF with bound radioactive vitamin B-12 and serum vitamin B-12 can be physically segregated from solid bentonite with adsorbed free radioactive vitamin B-12 and free serum vitamin B-12.

2. A method for separating free vitamin B-12 and a blood serum solution comprising combining an effective amount of bentonite with said solution to adsorb vitamin B-12 not bound by serum protein, and separating bentonite with said adsorbed vitamin B-12 relative to said solution.

3. A method in accordance with claim 2 wherein said bentonite is combined by dispersing it through said blood serum solution, and thereafter said solution is centrifuged to cause said relative separation.

4. An improved radioassay for vitamin B-12 including the steps of providing a first solution containing acid and a preselected amount of radioactive vitamin B-12; providing a blood serum sample; combining a second solution containing cyanide ions with said first solution and said blood serum sample; heating said last-named combination of solutions to reduce the binding capacity of the serum proteins to free vitamin B-12 therefrom; providing a third solution containing intrinic factor (IF) and human serum albumin; combining said third solution with a cooled combination of said first solution, second solution and serum sample following said heating step to competitively bind a portion of the radioactive vitamin B-12 and serum vitamin B-12 by said IF; and separating free radioactive vitamin B-12 and free serum vitamin B-12 from radioactive vitamin B-12 and serum vitamin B-12 bound by said IF.

5. The improved radioassy in accordance with claim 4 wherein the concentration of the components of said blood serum sample, second solution, and third solution are adjusted so that the volume used of each is the same.

6. The improved radioassay in accordance with claim 4 wherein said separation of free radioactive vitamin B-12 and free serum vitamin B-12 from bound radioactive and serum vitamin B-12 is executed by treating the combination of said first, second and third solutions and said serum sample with an effective amount of bentonite to adsorb free radioactive vitamin B-12 and free serum vitamin B-12.

7. The improved radioassay in accordance with claim 4 wherein said first solution contains acid derived from a member of the group consisting of hydrochloric acid, acetic acid and glycine buffer, and wherein the acid content is adjusted so that after reaction between said first solution, serum sample and IF, the pH is about 1.9 – 3.5.

* * * * *